Jan. 27, 1970 G. MERRILL Plant Pat. 2,966
PEACH TREE
Filed May 20, 1968
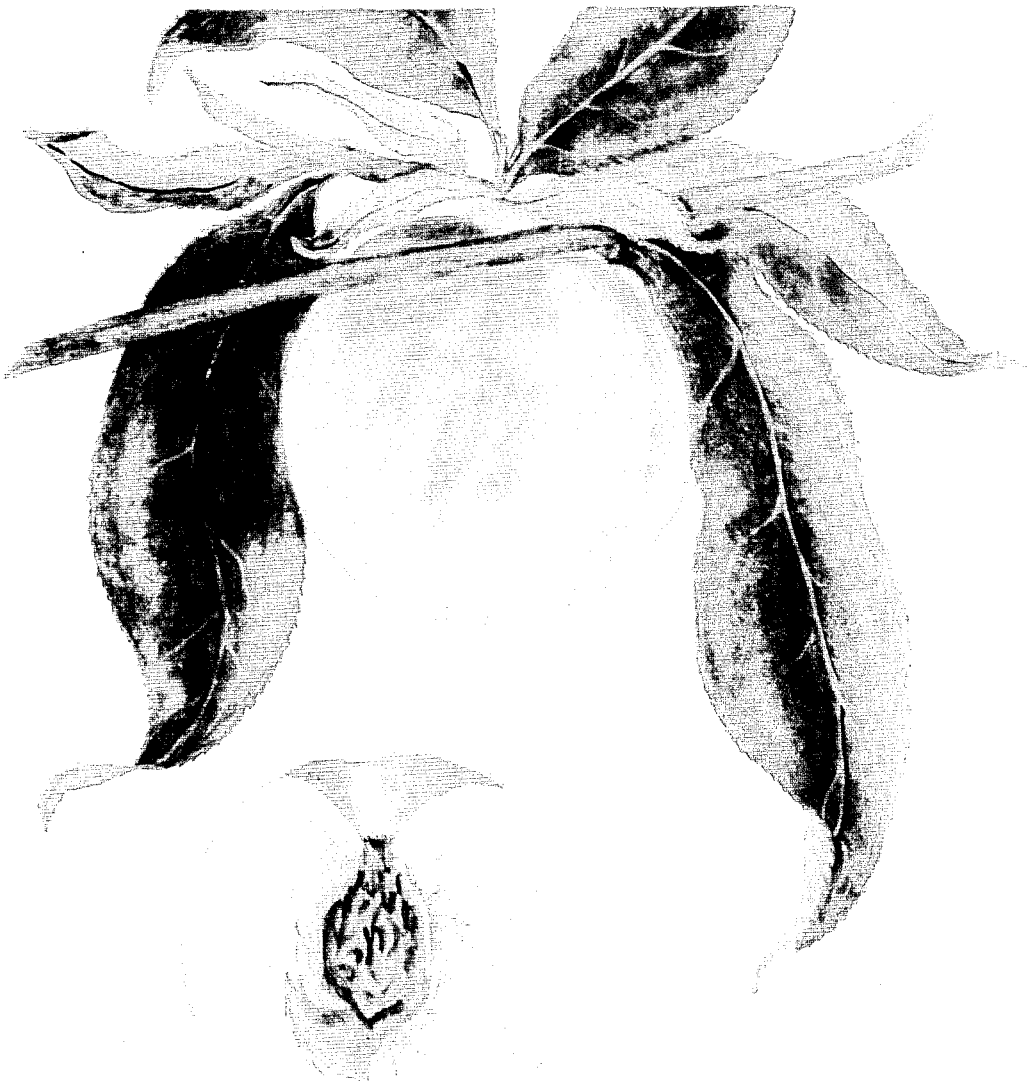
GRANT MERRILL
INVENTOR
Virgil L. Gerard
ATTORNEYS United States Patent Office Plant Pat. 2,966
Patented Jan. 27, 1970

2,966
PEACH TREE

Grant Merrill, Tulare County, Calif.
(416 N. Anderson Road, Exeter, Calif. 93221)

Filed May 20, 1968, Ser. No. 730,688
Int. Cl. A01h 5/08
U.S. Cl. Plt.—43 1 Claim The present invention relates to a peach tree and more particularly to a new and distinct variety thereof broadly characterized by its bearing fruit which is very highly colored with a scarlet red skin color and takes a polish when rubbed, and which is very firm for long distance shipment and for mechanical handling.

The instant variety most nearly resembles the Improved Pacifica (U.S. Plant Patent No. 2,425) but is distinguished therefrom and is an improvement thereon by reason of its ripening ten days to two weeks later, being firmer and having a scarlet red color and a skin which takes a polish when rubbed.

I originated the present variety of peach tree on a farm formerly owned by me at Red Bluff, Tehama County, Calif. in the following manner:

Blossoms of the Rodeo variety of peach (U.S. Plant Patent No. 1,097) were pollinated with pollen from a tree which was a cross of July Elberta (U.S. Plant Patent No. 15) with Leeton (unpatented). Seeds resulting therefrom were then planted and resulted on the present variety of peach tree.

The present variety was grafted to an Elberta (unpatented) tree on my farm at Exeter, Tulare County, Calif. and the tree and fruits and all other characteristics were exactly the same as on the original seedling.

The accompanying drawing is an oil painting of a characteristic twig of the subject peach tree bearing foliage and a mature fruit and additionally, showing a fruit of the subject variety divided on its suture plane to reveal flesh coloration and pit characteristics.

Referring more specifically to the pomological characteristics of this new and distinct variety of peach tree, the following has been observed under the ecological conditions prevailing at Exeter, Tulare County, Calif., and is an outline description thereof. All major color plate identifications are by reference to Maerz and Paul, Dictionary of Color, first edition.

TREE

General: Medium size, medium vigorous, productive, regular bearer.
Trunk: Medium stocky, shaggy.
Branches: Medium stocky, shaggy and gray on the older branches, less rough and brown on younger branches.
Leaves: Medium size, length, 4 to 7 inches long, 1 to 1⅞ inches wide, lanceolate, tip acuminate, medium thick, smooth and showing little of rugose condition, margins crenate; petiole medium length, medium diameter, deciduous.
Glands: Reniform, 2 to 4 mostly, green to yellow green, opposite, position at base leaf and on petiole; stipules on young leaves dropping off early, color dark green 32–L–12 to medium green 22–I–6 on leaflets and under side, a lighter green 20–I–4.

FLOWER BUDS

Medium size, round, free, pubescent.

FLOWERS

Medium size, pinkish-salmon in color, medium early about with July Elberta (U.S. Plant Patent No. 15), pollen moderately abundant, and in 1968, an early blooming year, first bloom February 29, full bloom March 6.

FRUIT

General: Eating to soft ripe when described.
Size: Variable, medium size, axially 2⅜ to 3 inches, transverse in suture plane 2¾ to 3⅛ inches, at right angles to suture plane 2½ to 3½ inches.
Form: Variable, generally globose with some flattening at stem and apical ends on some and suture ridge on some.
Suture ridge: Slight on some, pronounced on other fruits.
Ventral surface: Rounded.
Dorsal surface: Rounded.
Cavity: Abrupt, elongated in suture plane with suture showing on both sizes, cavity depth average ¾ inch, breadth ¾ to 1 inch, color yellow with red where exposed to the sun.
Base: Retuse.
Apex: Mucronate, pistil point apical, very small.
Stem: Length ⅜ to ⅝, adhering to stone occasionally.
Skin: Medium thick, medium tender, tenacious to flesh, pubescence scant, short, when rubbed off the skin takes a polish, color medium yellow undercolor, 10–L–5 overlaid with a bright scarlet red over half the surface where exposed to even small amounts of sunlight, from light red 1–L–10 to medium red 5–L–11 to dark red streaks 8–J–6.
Flesh: Color, light yellow undertone 10–J–3 to medium yellow overtones 10–L–7 with dark red streaks near the stone and running into the flesh 7–H–6; amygdalin, moderate; juice, moderate; texture, firm meaty; fibers, moderate, fine, tender; ripens, evenly; flavor, good; aroma, distinct; eating quality, good.
Stone: Adheres to flesh; none on most, slight on immature fruit; fibers, moderate, short; size, generally small, length average 1³⁄₁₆ to 1⁷⁄₁₆, breadth ¾ to 1 inch, thickness ⁹⁄₁₆ to ⅞ inch; form, obovate; tip, cuspidate; base, generally straight; hilum, oval; apex, cuspidate; sides, some equal, some unequal; surface, irregularly furrowed throughout, pitted throughout; pits, vary greatly in size and shape.
Ridges: Rounded; ventral edge; thick with many fine furrows; dorsal edge, central furrow with ridge on each side; color, light brown 15–E–12, with dark brown spots 48–L–12; tendency to split slightly.
Use: Local fresh market and long distance shipment.
Shipping quality: Good.

Although the new variety of peach tree possesses the described characteristics under the ecological conditions prevailing at Exeter, Tulare County, Calif., having been first observed near Red Bluff, Tehama County, Calif., it is to be understood that variation of the usual magnitude in characteristics incident to the growing conditions, fertilization, pruning and pest control is to be expected.

Having thus described and illustrated my new variety of peach tree, what is claimed is:

1. A new and distinct variety of peach tree substantially as illustrated and described and being characterized by its bearing fruit with skin of extremely high scarlet red color which takes a polish when rubbed and which is firm for mechanical handling and for long distance shipment, and most nearly resembling the Improved Pacifica (U.S. Plant Patent No. 2,425) but distinguished therefrom in bearing fruit ripening ten days to two weeks later, which is firmer and which has skin of a bright scarlet red which takes a polish when rubbed.

No references cited.

ROBERT E. BAGWILL, Primary Examiner